United States Patent [19]

Teshima et al.

[11] 4,160,447
[45] Jul. 10, 1979

[54] DEVICE FOR DETECTING PARTICULAR POINT OF HUMAN BODY

[75] Inventors: Toru Teshima, Hadano; Yoshinori Uchiyama, Machido, both of Japan

[73] Assignee: Stanley Electric Co., Ltd., Tokyo, Japan

[21] Appl. No.: 798,002

[22] Filed: May 18, 1977

[30] Foreign Application Priority Data

May 20, 1976 [JP] Japan .................. 51/64152[U]
May 21, 1976 [JP] Japan .................. 51/65176[U]
Jun. 11, 1976 [JP] Japan .................. 51/76047[U]

[51] Int. Cl.² .................. A61B 5/05; A61H 39/02
[52] U.S. Cl. .................. 128/735
[58] Field of Search .............. 128/2.1 Z, 2.1 C, 2.1 B, 128/2 M

[56] References Cited

U.S. PATENT DOCUMENTS

| | | | |
|---|---|---|---|
| 2,379,955 | 7/1945 | Eilenberger | 128/2.1 Z |
| 2,736,313 | 2/1956 | Mathison | 128/2.1 Z |
| 3,207,151 | 9/1965 | Takagi | 128/2.1 R |
| 3,468,302 | 9/1969 | Cowell | 128/2.1 R |
| 3,866,600 | 2/1975 | Rey | 128/2.1 R |
| 3,894,532 | 7/1975 | Morey | 128/2.1 Z |
| 4,052,978 | 10/1977 | Eugenio | 128/2.1 Z |

FOREIGN PATENT DOCUMENTS 1126634  9/1968  United Kingdom .............. 128/2.1 R

*Primary Examiner*—Lee S. Cohen
*Attorney, Agent, or Firm*—Flynn & Frishauf

[57] ABSTRACT

A device for detecting the impedance of the skin of a human body as a change of electric current comprises a time limit circuit which permits actuation of the device only one time according to a signal detected. A searching bar is coupled to the time limit circuit and has a curved or bent portion near which a luminous element is disposed. This searching bar may have adjustable sensitivity.

6 Claims, 7 Drawing Figures

FIG. 4
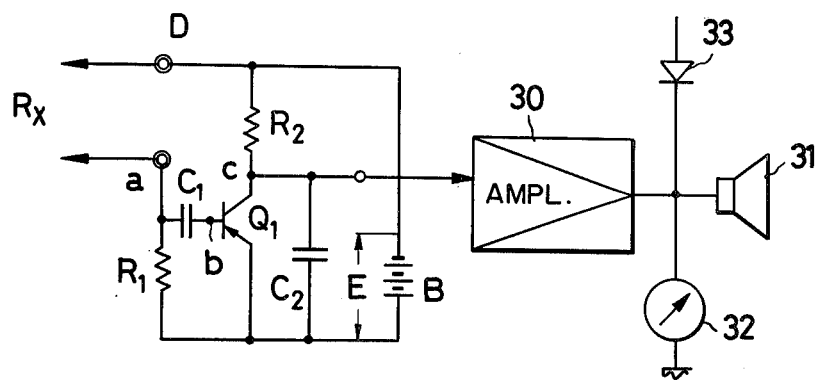
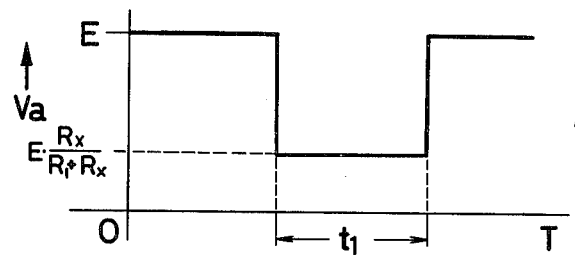
FIG. 5A
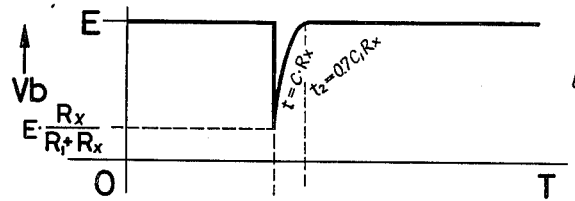
FIG. 5B
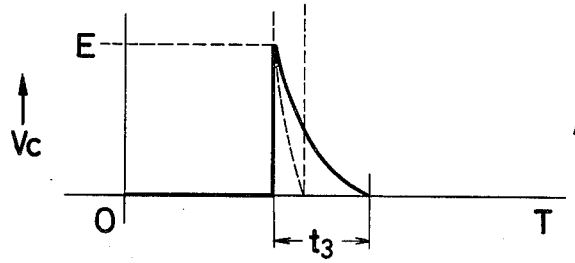
FIG. 5C

DEVICE FOR DETECTING PARTICULAR POINT OF HUMAN BODY

BACKGROUND OF THE INVENTION

The present invention relates to a device for detecting a particular point of a human body, and more particularly for detecting the impedance of the skin as a change of electric current.

In general, such a device for detecting a particular point of a human body uses a special cell or battery as its electric source in consideration of safety to the human body. (The particular point is a general term expressing portions that exist in several hundred portions of a human body and that correspond to important points of a particular circulating and reacting system which is different from the lymph system and nerve system in the human body and which comprises a main range including a part of an artery and a branch range including a part of a vein, the particular point being called a "tsubo spot" in Chinese medicine). However, in such a known device, a detecting portion of the device is continuously in contact with a particular point (tsubo spot of skin) of a human body, that is, a point of low impedance. Therefore, the cell is quickly consumed by the continuously generated detecting signals and therefore it is very uneconomical. In such a known device for detecting a particular body point, there is further used means for searching for a particular body point which is called a searching bar. This known searching bar is straight in shape and a probe is mounted on its leading end. There is also known an instrument for diagnosing ears which is classified as a device for detecting a particular body point and which is adapted electrically to search for a particular point existing in ears of a human body. The above known searching bar is also used in the instrument for diagnosing ears in the above shape. However, since the ear has a considerably complicated structure with undulations and the visual field of the inspector is intercepted by his hand supporting the searching bar of linear shape, it is very difficult for the inspector to visually confirm a particular point searched out by the searching bar. Accordingly, it not only becomes a factor of misreading by misleading a position of such a particular body point, but the medical treatment is interfered with. In general, since the searching bar is connected with a body of the device through the intermediary of a cord and the indicating part for indicating a reaction of the particular body point is provided at the body side, it is a defect that on searching, the inspector must watch both the searching portion and the indicating part of the body at the same time.

As mentioned above, the known instrument for diagnosing ears has a searching bar with a probe. The searching bar is grasped by the inspector and the probe provided on the bar is applied to the ear of the person to be inspected whereby the instrument is constituted to search for a particular point by passing a small electrical current in the auricular conch from the searching bar. However, the skin resistance of the person to be inspected has a personal difference depending upon age, condition or the like and therefore the reaction of a particular point may be changed on each search which is carried out by a searching bar which is adjusted to a fixed sensitivity. In general, the inspector carrying out such a diagnosis finds out four or five particular points and judges fairly these particular points according to the theory of entrails. However, if the sensitivity of the searching bar or the instrument for diagnosing ears is fixed as mentioned before, the reaction varies according to each person to be inspected notwithstanding that it is under the fixed condition, or varies according to each day to be inspected in spite of the same person being inspected, and therefore these inconveniences become a factor of misdiagnosis.

It is an object of the present invention to provide a device for detecting a particular point of a human body which does not have the defects mentioned above.

It is another object of the invention to provide a device for detecting a particular point of a human body having a time limit circuit in order to eliminate unnecessary exhaustion of its energy cell.

It is a further object of the invention to provide a device for detecting a particular point of a human body, in particular, an instrument for diagnosing ears, including a searching bar which is easy to use and observe and which has a small incidence of misdiagnosis.

SUMMARY OF THE INVENTION

According to a first aspect of the invention, there is provided a device for detecting a particular point of a human body which comprises means for detecting an impedance value of skin resistance as a function of electric current, and a time limit circuit which is actuated only one time according to the detecting signal.

According to another aspect of the invention, there is provided a searching bar used in an instrument for diagnosing ears, comprising a bent or curved end portion on which a probe is mounted, and a luminous element disposed near the bent or curved end to form an easily observed indicating portion.

BRIEF DESCRIPTION OF THE DRAWINGS

FIG. 4 is a circuit diagram showing a time limit circuit according to the invention; and FIGS. 5A–5C are graphical representations showing the relationship between voltage and time at points "a", "b" and "c", respectively, in the circuit of FIG. 4.

DETAILED DESCRIPTION

Figure 1:
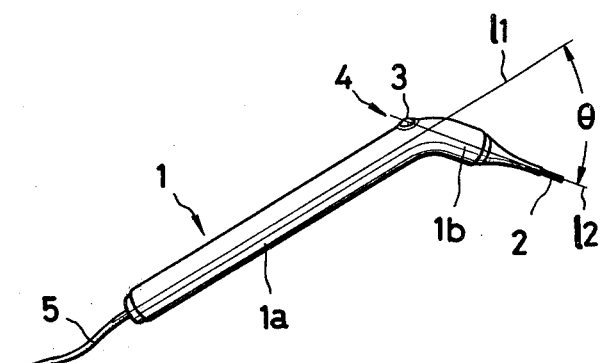
FIG. 1 is a pictorial view showing one embodiment of a searching bar according to the invention.

Referring now to FIG. 1, a searching bar 1 has a probe 2 mounted at the leading end thereof. The searching bar 1 of bar-like body shape has a grip portion 1a and a leading portion 1b angularly disposed relative to grip portion 1a. The leading portion 1b is formed to be capable of easily performing a visual confirmation of a particular body point when an inspector searches, for example, a particular point in an auricular conch by grasping the searching bar 1. Accordingly, for this purpose it is essential that the inspector's hand grasping the searching bar 1 does not obstruct his visual confirmation of the particular body point. In the embodiment shown in FIG. 1, an angle of about 45° is set as a bending angle between the longitudinal axis $l_1$ of the grip portion 1a and the longitudinal axis $l_2$ of the leading portion 1b. Near the leading portion 1b is disposed a luminous element 3, for example a luminous diode which lights up according to the current passing through, caused by the reaction at the particular body point to provide a visual indication portion 4. In this embodiment the indicating portion 4 is substantially placed on the longitudinal axis $l_2$ of the leading portion $1b$, that is, on the extension line of the probe 2 so that it is easily viewed. The searching bar 1 is connected to the body (not shown) by means of a cord 5. Since the above searching bar 1 is bent at its leading end the visual field of the inspector is not interrupted by his hand grasping the searching bar and the detection of the particular body point may be easily carried out even at a position hard to search, for example, a fold portion on the auricular conch, a complicated body portion or the like. Arrival at the particular body point may be confirmed immediately by luminescence of the indicating portion 4.

Figure 2:
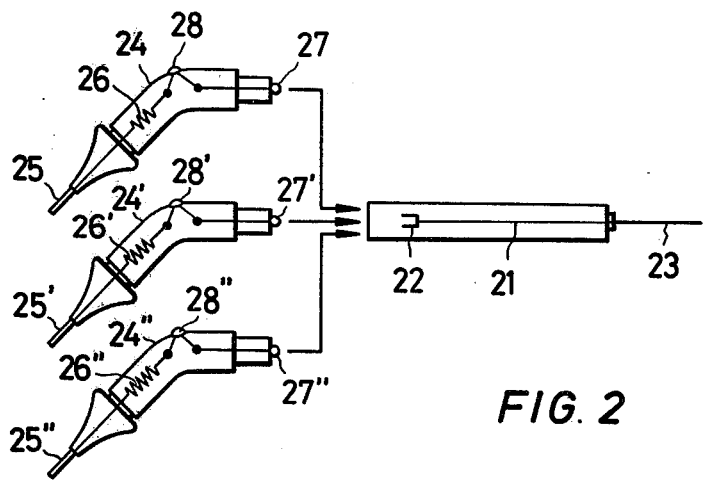
FIG. 2 is a pictorial view showing another embodiment of a searching bar according to the invention.

Referring to FIG. 2, there is shown a searching bar which is a combination type, particularly suitable for instruments for diagnosing ears. The searching bar comprises a cylindrical base 21 and one of adapters 24, 24′, and 24″. The base 21 contains a connector 22 connected to a cord 23 therein. The adapters 24, 24′, and 24″ are formed in a bend and probes 25, 25′ and 25″ are mounted on the respective leading portions of the adapters. In the adapters 24, 24′, and 24″ are contained respective electrical resistors 26, 26′, and 26″ of which each resistance value differs from the other in steps. Terminals 27, 27′, and 27″ are provided at the respective rear ends of the adapters. On each shoulder or bend portion of the adapters are disposed luminous elements 28, 28′, and 28″, respectively, which are incorporated in the circuit of each adapter. The terminals 27, 27′, and 27″ are constructed to fit in connector 22 to electrically connect the adapters to cord 23 when the adapter is fixed to the base 21.

As mentioned above, the searching bar for the instrument for diagnosing ears in the FIG. 2 embodiment is formed by fixing selectively one of the adapters 24, 24′, and 24″ to the base 21. Therefore, the inspector can vary the sensitivity of the searching bar according to the person to be inspected, upon searching the particular point of the latter.

Figure 3:
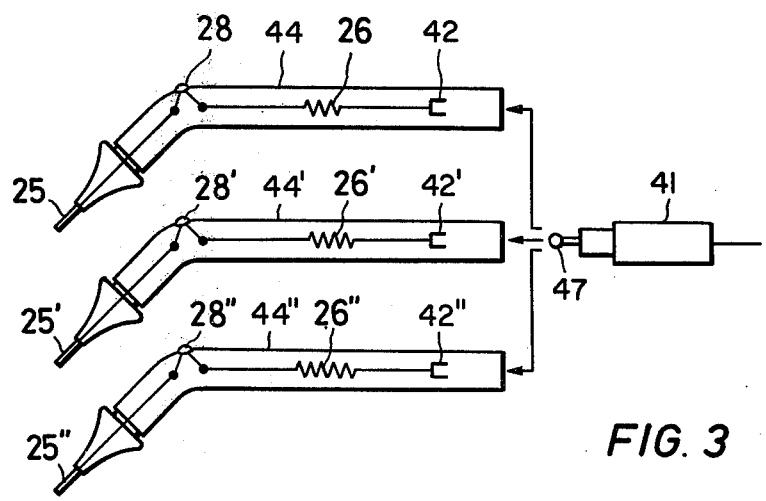
FIG. 3 is a pictorial view showing a further embodiment of a searching bar according to the invention.

Referring to FIG. 3, there is shown a searching bar in which connectors 42, 42′ and 42″ are mounted in respective adapters 44, 44′, and 44″ and a terminal 47 is provided on a base 41. In this embodiment, the other constructional features are similar to those of the embodiment shown in FIG. 2. In FIGS. 2 and 3, though the searching bar is shown for use with three adapters, it will be understood that the searching bar can be provided with more than three adaptors. Further, it is preferable that a suitable marking or indication is added to the adapters to distinguish them from each other.

Referring to FIG. 4, there is shown a time limit circuit adapted to avoid unnecessary exhaustion of the cell or battery B which is used as a power source of the device for detecting a particular body point according to the invention. To a plus side of the power source battery B is connected a portion for detecting a particular body point comprised of searching bar through the intermediary of a resistor $R_1$ and terminal "a". To a minus side of battery B is connected an abutting portion suitable for abutting to a human body. To the second side of the resistor $R_1$ is connected through a capacitor $C_1$ the base of a transistor $Q_1$. The emitter of transistor $Q_1$ is connected between the resistor $R_1$ and the power source B and the collector is connected to the minus terminal of the power source B through a resistor $R_2$. A time limit circuit is constructed by connecting capacitor $C_2$ between the first side of the resistor $R_2$ and the plus terminal of the power source B. A speaker 31 is connected to the output side of the capacitor $C_2$ through the intermediary of an amplifier 30. Further, an ammeter 32 and/or a luminous diode 33 may be connected to the output of amplifier 30.

In the circuit of FIG. 4, the voltage E of the power source B is introduced to the point "a" connected to the portion for detecting a particular body point through the resistor $R_1$. If $t_1$ expresses a time which permits the portion for detecting a particular body point to abut to the human body having an impedance $R_x$, the voltage Va at the point "a" is expressed by the following equation (see FIG. 5).

$Va = E \cdot (R_x/R_1 + R_x)$

Although the voltage Vb at the point "b" is usually equal to the voltage E, it drops down to the voltage of the point "a" at the beginning of the time $t_1$ when the portion for detecting a particular body point is applied to a certain position of the human body at which the impedance becomes Rx, and returns to the initial voltage of Vb=E according to variation of time constant $t_2 = 0.7 \cdot C_1 \cdot Rx$ which is decided by the resistance value Rx and the capacitance of the capacitor $C_1$. See FIG. 5B.

The current flows to the base of the transistor $Q_1$ according to the variation of the voltage Vb of the above mentioned point "b", and therefore in proportion to the degree of amplification of the transistor $Q_1$, the current flows from the emitter to the collector.

Accordingly, when the transistor $Q_1$ is turned on the voltage Vc at the point "c" rises up to the voltage E and the voltage Vc lowers down to 0 volts according to a time constant $t_3 = 0.7 \cdot C_2 \cdot R_2$ which is decided by the resistor $R_2$ and the capacitor $C_2$. Consequently, the time constant $t_3$ showing a fall time of the output voltage from the point "c" is decided by the resistor $R_2$ and the capacitor $C_2$ in spite of the length of the time constant $t_1$. Thus, a time limit circuit is constituted.

Further, though the time when the transistor $Q_1$ is turning on is decided by the capacitance of the capacitor $C_1$ the maximum value of the time is limited by the impedance $R_x$ of the human body (usually about 20 kΩ–50 kΩ).

Even if the detecting portion is continued to be applied to the human body, that is, even if the time $t_1$ is lengthened, since the transistor $Q_1$ becomes "ON" only for one time at the initial stage of the time $t_1$, the current thereafter does not flow in the testing circuit under the action of the time limit circuit.

The amplifier 30 is actuated by the output from point "c" to generate the detecting sound from the speaker 31. At the same time, indication is carried out by the meter 32 and/or the lighting of a luminous diode 33 whereby the user is informed that the position of the particular point, for example, a tsubo spot of the human body, has been detected. Further, in order to heighten safety to the human body, the power voltage shall be DC 12–18V, and the value of the resistor $R_1$ shall be more than 200 kΩ.

Accordingly, since the current passing to the human body through the resistor $R_1$ and the detecting portion is less than 60 μA, even if Rx=0 it does not have a great influence upon the exhaustion of the cell or battery B. Because the current consumed is 1 mA in the case of a meter and 5 mA–30 mA in the case of luminous diode, even if this current is used only for the time fixed by the $t_3$, the time cell is very slight depleted in respect to its exhaustion and it is economically utilized.

It is further understood by those skilled in the art that the foregoing description is a preferred embodiment of the disclosed device and that various changes and modifications may be made in the invention without departing from the spirit and scope thereof.

What is claimed is:

1. A device for detecting a particular point of a human body comprising:
   a searching probe adapted to selectively contact different points of a human body for detecting an impedance value of skin resistance as a function of electric current flowing through the human body;
   a source of power (B);
   means (D) for stationarily connecting a first pole of said power source to the skin of the human body;
   a first resistor ($R_1$) connecting a second pole of said power source to said probe;
   a first capacitor ($C_1$), one terminal of which is coupled between said first resistor ($R_1$) and said probe;
   a transistor ($Q_1$) having a base connected to the other terminal of said first capacitor; an emitter coupled to said second pole of said power source and a collector;
   a second resistor ($R_2$) coupling said collector to said first pole of said power source;
   a second capacitor ($C_2$) coupled between said collector and emitter of said transistor; and
   indicating means coupled to said collector of said transistor, said indicating means including at least a luminous diode for indicating a change in impedance detected by said searching probe;
   said transistor, first and second resistors and first and second capacitors comprising a time limit circuit for permitting substantially immediate actuation of said indicating means only one time immediately responsive to an impedance change detecting signal from said searching probe, said time limit circuit cutting off the supply of electrical current from said power source to said searching probe a predetermined period of time after generation of said detecting signal.

2. A device according to claim 1, wherein said searching probe generates said detecting signal responsive to detecting a predetermined impedance value of skin.

3. A device according to claim 1 wherein said indicating means comprises an amplifier coupling said collector of said transistor to said luminous diode.

4. A device according to claim 3 further comprising a meter coupled to the output of said amplifier for indicating said change in impedance by deflection of a meter needle.

5. The device according to claim 3 further comprising audible indicating means coupled to the output of said amplifier for audibly indicting a change in impedance detected by said searching probe.

6. A device according to claim 1 further comprising audible indicating means coupled to said collector of said transistor for audibly indicating a change in impedance detected by said searching probe.

* * * * *

UNITED STATES PATENT AND TRADEMARK OFFICE
CERTIFICATE OF CORRECTION

PATENT NO. : 4,160,447

DATED : July 10, 1979

INVENTOR(S) : Toru TESHIMA et al

It is certified that error appears in the above-identified patent and that said Letters Patent are hereby corrected as shown below:

```
Column 1, line 44, change "misreading by misleading a"
          to --misdiagnosis by misreading the--;
Column 4, line 19, after "the time" insert --period--;
Column 5, line 1, change "t_3, the time cell" to
          --time t_3, the cell--.
```

Signed and Sealed this

Eighteenth Day of March 1980

[SEAL]

Attest:

SIDNEY A. DIAMOND

Attesting Officer

Commissioner of Patents and Trademarks